United States Patent [19]

Gribi

[11] Patent Number: 4,836,853

[45] Date of Patent: Jun. 6, 1989

[54] ALGIN BASED DENTAL IMPRESSION MATERIAL CONTAINING BIOCIDAL COMPONENT

[75] Inventor: Hans-Peter K. Gribi, Uznach, Switzerland

[73] Assignee: Dentsply GmbH, Dreieich, Fed. Rep. of Germany

[21] Appl. No.: 217,113

[22] Filed: Jul. 8, 1988

Related U.S. Application Data

[63] Continuation of Ser. No. 922,930, Oct. 24, 1986, abandoned.

[51] Int. Cl.$^4$ .......................... A61K 6/10; A61C 9/00
[52] U.S. Cl. .................................. 106/35; 106/38.23; 106/205; 106/209; 264/16; 264/222; 264/DIG. 30; 424/409; 424/411; 433/214; 523/109
[58] Field of Search ..................... 106/35, 38.23, 205, 106/209; 260/998.11; 424/405, 409, 411; 433/214, 217.1, 226; 523/109; 264/16, 222, DIG. 30

[56] References Cited

U.S. PATENT DOCUMENTS

| | | | |
|---|---|---|---|
| 3,836,669 | 9/1974 | Dadekian | 252/106 |
| 3,845,216 | 10/1974 | Brink et al. | 424/329 |
| 3,850,864 | 11/1974 | Emerson | 260/17.2 |
| 3,868,340 | 2/1975 | Keegan et al. | 106/35 |
| 3,888,947 | 6/1975 | Stephenson et al. | 260/501.11 |
| 3,964,164 | 6/1976 | Hesselgren | 433/217.1 |
| 4,060,421 | 11/1977 | Yoshtkawa et al. | 106/35 |
| 4,073,888 | 2/1978 | Snyder | 514/643 |
| 4,182,829 | 1/1980 | Walkowiak et al. | 528/75 |
| 4,287,323 | 9/1981 | Tefertiller et al. | 525/404 |
| 4,315,779 | 2/1982 | Heyd et al. | 106/35 |
| 4,339,279 | 7/1982 | Hesselgren | 106/35 |
| 4,394,172 | 7/1983 | Scheuble | 106/38.5 D |
| 4,404,296 | 9/1983 | Schapel | 523/109 |
| 4,407,984 | 10/1983 | Ratcliffe et al. | 523/115 |
| 4,444,790 | 4/1984 | Green et al. | 424/329 |
| 4,450,174 | 5/1984 | Green et al. | 424/329 |
| 4,466,936 | 8/1984 | Schapel | 264/225 |
| 4,543,372 | 9/1985 | Watanabe et al. | 106/35 |

FOREIGN PATENT DOCUMENTS

| | | |
|---|---|---|
| 871771 | 5/1971 | Canada . |
| 983190 | 2/1976 | Canada . |
| 1123547 | 5/1982 | Canada . |
| 1143890 | 3/1983 | Canada . |
| 1179094 | 12/1984 | Canada . |
| 1106524 | 8/1987 | Canada . |
| 1106525 | 8/1987 | Canada . |
| 0057839 | 8/1982 | European Pat. Off. . |
| 0053442 | 9/1985 | European Pat. Off. . |
| 188040 | 7/1986 | European Pat. Off. . |
| 0195224 | 9/1986 | European Pat. Off. . |
| 0051691 | 10/1986 | European Pat. Off. . |
| 2131964 | 11/1977 | Fed. Rep. of Germany . |
| 2419887 | 7/1982 | Fed. Rep. of Germany . |
| 3423567 | 1/1986 | Fed. Rep. of Germany . |
| 936091 | 9/1963 | United Kingdom . |

OTHER PUBLICATIONS

*Hackh's Chemical Dictionary*, McGraw Hill Book Co., (4th Ed., 1969), p. 256.
Lonza Information Sheet re Bardac 2250, 2280.
Merck Index, p. 293, abstract 2057.
Bibliographe-Biocidal Agents in General, especially Bardac-22.

*Primary Examiner*—Paul Lieberman
*Assistant Examiner*—Linda D. Skaling
*Attorney, Agent, or Firm*—David E. Wheeler; Edward J. Hanson, Jr.

[57] ABSTRACT

A dental impression composition comprising alginate material and biocidal component.

A method for reducing microorganism contamination in alginate dental impressions comprising preparing a mixture comprising alginate, water and biocide.

9 Claims, No Drawings

ALGIN BASED DENTAL IMPRESSION MATERIAL CONTAINING BIOCIDAL COMPONENT

This is a continuation division, of application Ser. No. 922,930, filed Oct. 24, 1986, now abandoned.

BACKGROUND OF THE INVENTION

This invention relates to alginate dental impression materials used for taking an impression of dentition and surrounding oral tissues. The primary object of the invention is to prevent dental impressions formed from alginate impression materials from spreading infectious disease organisms by providing biocidal properties.

For many years health care professionals have been concerned that their patients may be cross-infected with microorganisms from a diseased patient. To minimize this risk, they sterilize their instruments by autoclaving or ethylene oxide treatment, wear face masks and gowns, and exercise scrupulous cleanliness in their operating rooms and offices.

Dentistry poses an especially more accentuated risk to the health-care profession because the surgical field is the oral cavity which contains many strains of bacteria. Dental operations spread these throughout the orifice atmosphere, thereby exposing dentists and dental auxiliaries to possible infection. In recent years concern has deepened over spreading viral infections such as Hepatitis B, A.I.D.S., and herpes.

Despite dentists' best efforts to sterilize their instruments and hardware, there are certain sensitive dental materials which have heretofore been difficult and in some cases impossible to sterilize, because the heat or chemicals needed for sterility would adversely affect the material's primary function. Dental impression materials are an example of this—their primary function is to make an accurate replica of the oral tissues and thus they must be rubbery, dimensionally accurate and have good surface wetting properties. Any application of heat or unusual chemical activity to achieve sterility can cause them to distort, soften, stick to teeth and other surfaces or otherwise defeat their main purpose. This is especially a problem for alginate impressions which are hydrogels of calcium alginate and inert filler. These compounds can dehydrate rapidly, thus changing dimension; or if placed in an aqueous sterilizing solution they attract additional water, thus also changing dimension. As a consequence, normal dental impressions become contaminated or impregnated with bacteria and viruses from the patient, which can be spread to dental auxiliaries (assistants, technicians) who handle the impressions in the process of making casts, models and prosthesis.

It is known in the dental art that hydrocolloid materials of the agar type are kept in a warm condition between uses and thus provide ideal conditions for mold growth. It is a common practice to add a chemical preservative or fungicide to prevent such mold growth.

It also is known that hydrophilic polymer containing powders and pastes may be used as denture adherents and that the addition of antimicrobial agents may make an individual patient's denture more sanitary or less prone to offensive odor.

However, neither of the above prior art examples are intended to prevent cross-infection of disease organisms, nor do they apply to the alginate type of irreversible hydrocolloid impression material.

Some dental impression materials, such as silicone rubbers, are hydrophobic and relatively impervious to oral fluids and may be partially decontaminated by surface treatment, such as wiping with alcohol or immersing in an aqueous biocidal material. However, alginate impression materials are preferred for partial dentures, orthodontics, and many other dental procedures. These alginate impression materials are particularly prone to contamination because oral fluids may diffuse into them and remain unaffected by brief surface treatment. When formed into the impression the alginate materials tend to swell and distort if immersed in aqueous disinfectants or when the surfaces of the impression are treated.

OBJECTIVES

It is an object of the present invention to provide dental impression materials of the alginate type which are effective and accurate by today's standards, and yet are safe against transmitting disease organisms to dental auxiliaries, lab technicians, lab equipment, and possibly cross-infecting other patients.

It is another object of the invention to provide for the production of alginate dental impressions that are free of illness-causing microorganisms and will remain free of those organisms for prolonged periods of time.

It is a further object of the invention to provide alginate dental impressions that are free of and remain free of microbial contaminants and unpleasant odors during extended periods of storage and use.

Another object of the invention is to provide a method for making alginate dental impressions that reduces the risk of disease contamination between patient, dentist, dental auxiliaries and other patients.

SUMMARY OF THE INVENTION

By the present invention an alginate dental impression composition containing an effective biocidal component is provided. The provision provides biocidal effectiveness in the completed dental impression. This is accomplished without disrupting the physical/chemical features which make an impression material function efficaciously, as well as having low toxicity to humans and to oral tissue, and in its preferred forms provide effective bactericide, fungicide and virucide, properties to the dental alginate impression materials.

In one preferred embodiment the biocide can be included in the powdered precursor dental impression composition to which water is added. In another embodiment the biocide can be included in the water. In yet another embodiment biocidal ingredients can be added as part of the precursor composition, in the water and separately. The most preferred biocidal ingredient is didecyldimethyl ammonium chloride.

By another aspect of the present invention a method is provided to produce a dental impression having biocidal properties. By the method a mixing comprising alginate, water and biocide is prepared. Biocide is most preferably introduced into the mixture with the alginate as part of a solid precursor composition at least a portion of which is placed in a mixing vessel as a dry composition and to which water is added. The biocide may be introduced into the mixture with the water or separately.

The method of the present invention includes as an aspect forming a substantially uniform sol having biocidal properties, placing the sol in engagement with oral tissue of a human and forming a negative impression of the oral tissue, setting the sol and removing the set sol from engagement with the oral tissue and thereby obtaining a usable alginate dental impression having biocidal properties.

PREFERRED EMBODIMENT

By the present invention a biocidal agent is incorporated into dental impression materials of the alginate type to provide such impression materials for the first time with substantive biocidal properties. It is an important aspect of a preferred embodiment of the present invention that the biocidal agent be stable in the powdered dry alginate impression material while it is stored in warehouses, shipped and stored in the dental operatory prior to use. By another aspect of the invention the biocidal agent may be added with the liquid in the course of activating the alginic impression powder by mixing the liquid and powder to form a paste. Preferably the biocidal agent is broad spectrum both in the sense of being effective against bacteria, viruses and fungus, and with respect to disease causing or noxious organisms within each class. By biocidal agent or component it is meant an agent added at least in part specifically for its biocidal effect as contrasted to the usual ingredients that have been added in the past to alginate impression materials for dental applications.

Especially preferred alginate aqueous gels for taking orthodontic and partial denture impressions are based upon water soluble salts of alginic acid reacting with a setting reactant (calcium sulfate) to form an insoluble reactant (calcium alginate). This reaction takes place very quickly after mixing a powder containing the alginic acid salt and setting reactant with water. The dentist is provided more working time by the addition of a small quantity of a retarder (such as trisodium phosphate or tetrasodium pyrophosphate) to the powder. Thus the reaction to form an irreversible calcium alginate gel does not go to completion until the more active retarder has been completely reacted. The alginate gel which is formed has good rubbery properties or elasticity. A desired degree of firmness is imparted by fillers of fine particle size—such as diatomaceous earth; however other inert materials such as talc or clay may be used as well. A surface hardening agent may be added, usually a fluoride compound, to condition the gel surface and promote a harder model when a (positive) gypsum cast is made against the (negative) alginate impression. Another modifier which is frequently added is a nonvolatile, non-aqueous compound such as polypropylene glycol to prevent the fine powders from dusting during dispensing, measuring and mixing.

By dental impressions it is meant to include any negative impression formed of the dentition, mucousal surfaces, or underlying bone as may be needed in the practice of dentistry, including fixed and removable prosthodontics, restoratives and orthodontics (i.e. crowns, bridges, implants, complete and partial dentures, inlays, onlays, veneers and the like). By dentist it is meant to include general practice and specialists such as oral surgeons, orthodontists, prosthodontists, implantologists and the like. By dental auxiliaries it is meant to include those who assist the dentist in his office and those who fabricate prostheses at a separate facility from a dental impression and using indirect procedures. Dental or dentistry is meant to encompass the entire field of endeavor.

By precursor solid composition it is meant all of the solid ingredients that are combined with the liquid (water) to form the paste that then sets to form the dental impression. The precursor solid composition may contain liquid ingredients, waxy materials and other materials that are not themselves solids but when included in the precursor composition do not change the nature of the precursor composition from a solid to a liquid composition.

The biocide may be introduced in the precursor solid composition, in the liquid or separately. When the biocide is introduced in the liquid or separately, the biocide is all the same added up as an ingredient by weight percent in the precursor composition in calculating the quantities of ingredients to total 100% with the biocide included. Of course, when the biocide is in solution in the liquid, it is only the active biocidal ingredient that is considered in calculating the percent biocide. This makes the calculation the same whether the biocide is included in the powder precursor composition or the liquid that is to be added to form the gel. The biocide (biocidal component or biocidal agent) may be a single compound or a combination of compounds and other active ingredients. Biocidal active ingredients are to be counted in the calculations, but not non biocidally active diluents or other carrier or extender materials and the like.

Preferred alginate dental impression materials of the present invention have a composition in the following ranges:

|  | Preferred | More Preferred | Most Preferred |
|---|---|---|---|
| Soluble alginate | 5–30% | 5–20% | 10–15% |
| Setting reactant | 5–60 | 8–30 | 10–20 |
| Retarder | 0.1–30 | 0.5–10 | 0.8–3.0 |
| Filler | 30–80 | 40–70 | 45–65 |
| Surface hardening agent | 0–10 | 1–8 | 1.5–6 |
| Anti-dusting agent | 0–10 | 1–8 | 2–6 |
| Biocidal component | 0.01–10 | 0.3–6.5 | 0.5–3 |

Typically a preferred dental impression material using preferred specific ingredients would have a composition:

| Matrix reactants: | Potassium or sodium alginate | 5–30% |
|---|---|---|
| Setting reactant: | Calcium sulfate | 5–60 |
| Retarder: | Tetrasodium polyphosphate | 0.1–30 |
| Filler: | Diatomaceous earth | 30–80 |
| Hardener: | Potassium fluorotitanate | 0–10 |
| Anti-dust: | Polypropylene glycol | 0–10 |
| Biocidal component: | Didecyldimethyl Ammonium Chloride | 0.01–10 |

While a preferred general formulation of alginate using preferred specific ingredients is given above it is known that alginate impression materials have many variants and additives as are shown in the patent literature and elsewhere. The present invention has general applicability to the wide variety of alginate impression materials.

In normal dental practice, one part of a dry precursor solid alginate powder composition is mixed with two to three parts of water (by weight) to form a sol which is converted to a rubbery gel by an irreversible chemical reaction. By dry it is meant dry at normal ambient conditions. By solid precursor composition, it is meant as contrasted to the state after the activating water has been added to form a sol. The reaction is adjusted by correct proportioning of the ingredients to provide desired handling times, setting reaction, dimensional accuracy and fragility of the gel. Mixing, and water temperature are also important to providing a good dental impression under operatory conditions. These general considerations are those existent with the presently widely used alginate impression materials. The alginate impressions are also sensitive to storage conditions as they tend to shrink on drying or swell in warm humid conditions.

The preferred biocidal additive which is the subject of this invention preferably is effective against various types of microorganisms: bacterial, viral, and fungal. A biocide is generally destructive to many microorganisms and biocide as used in this application includes effectiveness against at least one microorganism. Preferably the biocide would have a broad spectrum of effectiveness against many disease-causing or deleterious organisms in more than one of the above classes; more preferably in all three classes of organisms.

The more preferred biocidal additives for alginate impression materials is one chosen from the group including water soluble and/or water dispersible quaternary ammonium compounds, bisguanidine compounds, dialkyl quanternary compounds, quinoline compounds, and substituted phenols and mixtures thereof.

A most preferred biocidal additive found for alginate impression materials is Didecyldimethyl ammonium chloride. Didecyldimethyl ammonium chloride stands out as a most desirable biocidal material for use in the present invention because it has been found to retain wide spectrum effectiveness against multiple classes of microorganisms and especially those known to be of great concern today, including Hepatitis B, herpes, and A.I.D.S. Didecyldimethyl ammonium chloride is extraordinary in not materially affecting the dry powder alginate dental impression materials reaction with water to form a rubbery gel of suitable handling, hardening and physical properties needed in such impression materials in compliance with the American Dental Association and other regulatory standards.

Didecyldimethyl ammonium chloride may be added to the dry alginate impression powder and/or added to the water with which the powder is to be mixed. A formula for a useful liquid concentrate of the biocidal additive is:

| | |
|---|---|
| Didecyldimethyl ammonium chloride | 50% |
| Water | 30% |
| Isopropanol | 20% |

Work time, set time, dimensional accuracy and tear strength are not significantly deleteriously affected by the effective concentrations of didecyldimethyl ammonium chloride additive and in particular in the 0.03 to 6.5% range and especially the 0.5–3% range. By contrast, the addition of similar quantities of other biocidal agents, such as glutaraldehyde (as shown in Example 30) may interfere with the delicate chemical setting reaction of the alginate materials and be deleterious to the taking of an accurate dental impression to be ineffective, poorly effective or less effective as a biocidal agent (see Examples 11–25).

Test show that didecyldimethyl ammonium chloride is effective within a short time after mixing the alginate against concentrates of the following common oral microorganisms: staphylococcus aureus, streptococcus pyogenes, escherichia coli, pseudomonas aeruginosa, and Candida Albicans. This is especially true of the most preferred concentration of the active ingredient—didecyldimethyl ammonium chloride. Lesser concentrations and in particular less than the more preferred concentrations require an excessive time (longer than the setting reaction) to be effective against oral microorganisms such as staphylococcus aureus in the usual dental applications where time is so important. Didecyldimethyl ammonium chloride is very effective at the most preferred concentration level of 0.5% against Hepatitis B virus, HTLV III/LAV (A.I.D.S.) virus, and some of the Herpes strains.

The preferred content of Biocidal component in an alginate impression material has been established in the present invention as 0.01 to 10% by weight based on the weight of the alginate precursor (the alginate without the activating water) with the weight of the biocide included in the calculation even if the biocide or the biocide additive, agent or component (which may be made up of two or more biocide or anti microbial agents or compounds) is added to or with the liquid or is to be added separately from the liquid and the precursor. More preferably the biocide content is 0.3 to 6.5% and most preferably 0.5 to 3% by weight.

While less preferred, other biocidal materials may be used in accordance with the present invention. For example, those previously mentioned are examples of such other biocides as illustrated in the Examples. Other quaternary ammonium salts are also in this preferred category. Other dialkyl quaternary compounds are also in a preferred category. An example of such another quaternary ammonium compound as shown in the Examples is bisdequalinium acetate (BDQA) which also establishes another preferred category, those biocides containing quinoline groups.

Examples of the preferred bisguanidine biocides are 1, 6-di-(4-chlorophenyldiguanido) hexane dihydrochloride and 1, 6-di-(4-chlorophenyldiguanido) hexane diacetate (Hibtane acetate) of Examples 24 and 25. Example of preferred substituted phenol biocides are the thymol and eugenol of Examples 20 and 21 and 22 and 23 respectively. Examples of a preferred quaternary compound biocides are N-Cetylpyridinium chloride of Examples 16 and 17, and N-Cetyl-N,N,N-Trimethylammonium bromide of Examples 18 and 19.

By another aspect of the present invention a method is provided for reducing microorganism contamination in alginate dental impressions prepared from mixtures comprising alginate, water and biocide. The biocide is preferably introduced into the mixture with the alginate in a solid precursor composition at least portion of which is placed in a mixing vessel as a dry composition to which at least a portion of the water is added while the alginate precursor is still a powder to provide a means for forming a sol. The biocide may also be introduced into the mixture with the water with the alginate being placed in a mixing vessel as part of a dry precursor composition and the water with the biocide being added.

After a substantially uniform sol is formed, the sol is engaged with oral tissue of a human, forming a negative impression of the oral tissue. The sol then sets, is removed from engagement with the oral tissue and thereby a usable alginate dental impression is obtained.

By alginate material it is meant to include both the precursor solid composition and the set dental impression formed therefrom. By dental impression composition it is meant to include the precursor solid composition with the biocidal agent included in the dry powder composition and the set dental impression.

The invention will be more fully understood in conjunction with the following examples thereof, which examples merely are illustrative and should not be considered to be limitative of the materials and procedures employed in practicing the invention.

EXAMPLE 1

Alginate dental impression material was formulated to contain 0.5% Didecyldimethyl ammonium chloride (DDDMAC) by adding a commercially available water solution of DDDMAC (Bardac - 22 from Lonza) which had the following composition:

| | |
|---|---|
| DDDMAC | 50% |
| Water | 30% |
| Isopropanol | 20% |
| 0.60 gm of the DDDMAC solution were diluted to 37 ml with distilled water. | |

This water solution was then added to 16.5 gm of the alginate dental impression material previously placed in a plastic mixing bowl and mixed with a spatula according to the directions on the alginate impression material package until a uniform paste was achieved.

The effectiveness of the biocidal activity was then determined with a diffusion screening test: freshly mixed material was poured on a sterile, flat source in a thickness of 2 mm and allowed to harden. Discs 10 mm in diameter were then punched and placed on a hardened suspension of bacillus subtilis (bacillus subtilis, spore suspension for the inhibitor test, Merck 10649, Lot No.: 314633) in trypticase soy-agar and incubated for 24 hours at 37° C. An inhibition zone of 21 mm in diameter was measured.

EXAMPLES 2-5

The procedure of Example 1 was repeated except the concentration of the didecyldimethyl ammonium chloride was varied from 0 to 0.5% in the set product. The results are shown in the table below:

| Example No. | 2 | 3 | 4 | 5 |
|---|---|---|---|---|
| Concentration of Didecyldimethyl Ammonium Chloride in Set Product | 0% | 0.01% | 0.03% | 0.05% |
| Diameter of Inhibition Zone in mm | 0 | 13-14 | 15-16 | 19-21 |

EXAMPLES 6-8

Precursor solid compositions were formulated by adding the DDDMAC solution of Example 1 to an alginate impression material by adding the DDDMAC to polypropylene glycol (PPG) having a molecular weight of 2,000 (4% by weight) and filler (diatomaceous earth 61.75% by weight) to yield the concentrations of DDDMAC given below. When mixed with water these provided concentrations of DDDMAC as also shown below.

| Example No. | 6 | 7 | 8 |
|---|---|---|---|
| Alginate, gram | 200 | 200 | 200 |
| DDDMAC, gram | 6.49 | .65 | .13 |
| % DDDMAC in mixed impression | .48 | .05 | .01 |

| Example No. | 6 | 7 | 8 |
|---|---|---|---|
| material | | | |

The combined DDDMAC and PPG were added to the filler along with vigorous stirring by hand to provide a substantially even distribution. A fluffy powder was obtained. This was then added to a 2 liter-powder flask equipped with a metal spiral spring along with:

3.5% by weight magnesium oxide
1.3% by weight pentasodium triphosphate
4.5% by weight potassium fluorotitanate
0.75% by weight sodium fluoride
0.20% by weight organic pigment
12% by weight calcium sulfate dihydrate
and the flask was turned for 30 minutes after which 12% by weight triethanolammonium alginate was added. The percents by weight are given based on 100% excluding the biocide to give relative proportions but were adjusted to give 100% including the biocide.

Discs were formed in the manner of Example 1. Biocide was not present in the water. Rather, prior to mixing the water was seeded with Staphylococcus Aureus (ATCC-Nr. 6538) in an amount to give about 1 million colonies/gram of product. when the discs hardened they were transferred to hermetically sealed polyethylene bags for the periods of time given below. Subsequently the material was homogenized, diluted and the number of colony forming units counted according to USP XXI (antimicrobial effectiveness test).

TABLE 3

| | Antimicrobial Effectiveness | | |
|---|---|---|---|
| Storage Time/Example # | 6 | 7 | 8 |
| Colonies at beginning | 1,500,000/g | 1,500,000/g | 1,500,000/g |
| Colonies after 30 min. exposition | <10/g | 10,200/g | 119,000/g |
| Colonies after 6 hrs. exposition | <10/g | <10/g | 19,000/g |
| Colonies after 24 hrs. exposition | <10/g | <10/g | 3,200/g |

This shows DDDMAC to be antimicrobially effective in as little as 30 minutes after mixing.

EXAMPLE 9

The shelf stability of the precursor solid composition of Example 6 was tested by storing the powder at 60° for one and two weeks and then comparing gel and set times after mixing with water as described in Example 1.

TABLE 4

| 2 Repetitions | 0 Days | 7 Days | 14 Days |
|---|---|---|---|
| Gel Time | 2 min. 12 sec. | 2 min. 29 sec. | 2 min. 30 sec. |
| Gel Time | 2 min. 13 sec. | 2 min. 30 sec. | 2 min. 32 sec. |

The biocide did not significantly alter gel or set times.

EXAMPLE 10

Example 6 was repeated, but instead of only Staphylococcus aureus different microbial strain were tested separately as indicated below at the exposition times given:

|  | Colonies at beginning | After 10 min. | After 30 min. |
|---|---|---|---|
| *Staphylococcus Aureus* | 2,400,000/g | <10/g | <10/g |
| *Streptococcus Pyogenes* | 940,000/g | <10/g | <10/g |
| *Escherichis Coli* | 3,200,000/g | 30/g | <10/g |
| *Pseudomonas Aeriginjosa* | 1,800,000/g | 20/g | <10/g |
| *Candida Albicans* | 840,000/g | <10/g | <10/g |

EXAMPLE 11–25

Examples 11–25 were prepared and tested according to the procedure of Example 7 except as indicated below.

The biocides of Examples 16–25 were solid and added to the 2 liter-powder flask with the 1st charge of ingredients. Examples 11, 12, 13, 16, 18, 20, 22 and 24 were stored (aged) as a dry precursor solid composition at 60° C. for 2 weeks before testing. Examples 14, 15, 17, 19, 21, 23 and 25 were not stored but were tested immediately after mixing with water to form the sol paste with the evaluation delay indicated in the chart below.

| DISINFECTANTS .5% OF ACTIVE INGR IN SET ALGINATE | TIME FROM START OF MIXING (MIN) | STAPH. AUREUS Colonies/g | STREPT. PYOG. Colonies/g | E. COLI Colonies/g | PS. AERUGINOSA Colonies/g | C. ALBICANS Colonies/g |
|---|---|---|---|---|---|---|
| EXAMPLE 11 POTASSIUM ALGINATE | DDDMAC | | | | | |
| | 0 | 2,100,000 | 4,800,000 | 1,100,200 | 9,800,000 | 6,200,000 |
| | 10 | <10 | <10 | <10 | <10 | <10 |
| | 30 | <10 | <10 | <10 | <10 | <10 |
| EXAMPLE 12 SODIUM ALGINATE | DDDMAC | | | | | |
| | 0 | 2,1000,000 | 4,800,000 | 1,100,000 | 9,800,000 | 6,200,000 |
| | 10 | <10 | <10 | <10 | 40 | 28,000 |
| | 30 | <10 | <10 | <10 | 10 | 40 |
| EXAMPLE 13 TRIETHANOLAMMONIUM ALGINATE | DDDMAC | | | | | |
| | 0 | 2,100,000 | 4,800,000 | 1,100,000 | 9,800,000 | 6,200,000 |
| | 10 | <10 | <10 | <10 | 140 | <10 |
| | 30 | <10 | <10 | <10 | 60 | <10 |
| EXAMPLE 14 TRIETHANOLAMMONIUM ALGINATE | DDDMAC | | | | | |
| | 0 | 2,400,000 | 4,800,000 | 1,100,000 | 9,300,000 | 6,200,000 |
| | 10 | <10 | <10 | <10 | 14,000 | 20 |
| | 30 | <10 | <10 | <10 | 150 | <10 |
| EXAMPLE 15 TRIETHANOLAMMONIUM ALGINATE | DDDMAC | | | | | |
| | 0 | 2,400,000 | 940,000 | 3,200,000 | 1,800,000 | 840,000 |
| | 10 | <10 | <10 | 30 | 20 | <10 |
| | 30 | <10 | <10 | <10 | <10 | <10 |
| EXAMPLE 16 TRIETHANOLAMMONIUM ALGINATE | N—CETYLPYRIDINIUM CHLORIDE | | | | | |
| | 0 | 2,100,000 | 4,800,000 | 1,100,000 | 9,800,000 | 6,200,000 |
| | 10 | 20 | <10 | <10 | >500,000 | >500,000 |
| | 30 | <10 | <10 | <10 | 10,000 | 32,000 |
| EXAMPLE 17 TRIETHANOLAMMONIUM ALGINATE | N—CETYLPRIDINIUM CHLORIDE | | | | | |
| | 0 | 2,100,000 | 4,800,000 | 1,100,000 | 9,800,000 | 6,200,000 |
| | 10 | <10 | <10 | 20 | 80,000 | 39,000 |
| | 30 | <10 | <10 | <10 | 22,000 | 11,000 |
| EXAMPLE 18 TRIETHANOLAMMONIUM ALGINATE | N—CETYL-NNN—TRI-METHYLAMMONIUM BROMIDE | | | | | |
| | 0 | 2,100,000 | 4,800,000 | 1,100,000 | 9,800,000 | 6,200,000 |
| | 10 | 20 | 40 | 60 | 150,000 | 28,000 |
| | 30 | <10 | <10 | <10 | 44,000 | 10 |
| EXAMPLE 19 TRIETHANOLAMMONIUM ALGINATE | N—CETYL-NNN—TRI-METHYLAM.BROMIDE | | | | | |
| | 0 | 2,100,000 | 4,800,000 | 1,100,000 | 9,200,000 | 6,200,000 |
| | 10 | <10 | <10 | <10 | 101,000 | 45,000 |
| | 30 | <10 | <10 | <10 | 29,000 | 15,000 |
| EXAMPLE 20 TRIETHANOLAMMONIUM ALGINATE | THYMOL | | | | | |
| | 0 | 2,100,000 | 4,800,000 | 1,100,000 | 9,800,000 | 6,200,000 |
| | 10 | 3,100 | 11,000 | 4,800 | 180,000 | 420,000 |
| | 30 | <10 | 3,000 | 1,200 | 19,000 | 80,000 |
| EXAMPLE 21 TRIETHANOLAMMONIUM ALGINATE | THYMOL | | | | | |
| | 0 | 2,100,000 | 4,800,000 | 1,100,000 | 9,800,000 | 6,200,000 |
| | 10 | <10 | 41,000 | 18,000 | 500,000 | 110,000 |
| | 30 | <10 | 6,000 | 1,100 | 82,000 | 23,000 |
| EXAMPLE 22 TRIETHANOLAMMONIUM ALGINATE | EUGENOL | | | | | |
| | 0 | 2,100,000 | 4,800,000 | 1,100,000 | 9,800,000 | 6,200,000 |
| | 10 | 2,100 | 14,000 | 1,400 | 120,000 | 84,000 |
| | 30 | <10 | 1,300 | 210 | 52,000 | 44,000 |
| EXAMPLE 23 TRIETHANOLAMMONIUM ALGINATE | EUGENOL | | | | | |
| | 0 | 2,100,000 | 4,800,000 | 1,100,000 | 9,800,000 | 6,200,000 |
| | 10 | <10 | 3,500 | 2,100 | >500,000 | 24,000 |
| | 30 | <10 | 2,900 | 900 | 2,100 | <10 |
| EXAMPLE 24 TRIETHANOLAMMONIUM ALGINATE | CHLOROHEXIDINE | | | | | |
| | 0 | 2,100,000 | 4,800,000 | 1,100,000 | 9,800,000 | 6,200,000 |
| | 10 | <10 | <10 | <10 | 16,000 | 74,000 |
| | 30 | <10 | <10 | <10 | 1,200 | 3,600 |
| EXAMPLE 25 TRIETHANOLAMMONIUM ALGINATE | CHLOROHEXIDINE | | | | | |
| | 0 | 2,100,000 | 4,800,000 | 1,100,000 | 9,800,000 | 6,200,000 |
| | 10 | <10 | <10 | <10 | 500,000 | 21,000 |
| | 30 | <10 | <10 | <10 | 92,000 | 5,200 |

A. The following conclusions can be drawn from the 10 minutes values, which are of particular importance. No significant difference is considered to exist between aged samples and the unaged samples. DDDMAC is by far the best biocide. Compare especially the two most resistant strains Ps. Aerug and C. Albicans. In order of diminishing apparent effectiveness for the tested parameters DDDMAC >> Chlorohexidine >> other quaternary ammonium salts >> substituted phenols

EXAMPLE 26-33

To test for the effect of various biocidal additives on the shelf stability of the alginate impression material the procedure of Example 7 was repeated except as indicated below.

All of the non liquid biocide ingredients were charged to the 2 liter-powder flask with the first charge, i.e., before the alginate was added. These were all of the biocides except the DDDMAC and glutaraldehyde.

| ADDITIVES: | |
|---|---|
| DDDMAC (BARDAC-22 3.42%) | 50% DIDECYLDIMETHYLAMMONIUM CHLORIDE |
| GLUTARALDEHYDE 6.86% | 30% WATER |
| CHLORHEXIDINE A.C. 1.71% (HIBITANE ACETATE) | 20% ISOPROPANOL |
| | 25% AQU. SOLUTION |
| N—CETYL-N,N,N—TRIMETHYL AMMONIUMBROMIDE | |
| N—CETYL-PYRIDINIUM CHLORIDE H$_2$O | } 1.71% |
| THYMOL | |
| EUGENOL | |

Concentration of disinfectants is such as to be .5% of active ingredient in set product (15.2 g alginate powder/37 ml water).

| | GEL TIME | | | GEL TIME | | |
|---|---|---|---|---|---|---|
| | 0 W. | W. 60° C. | 2 W. 60° C. | 0 W. | 1 W. 60° C. | 2 W. 60° C. |
| EXAMPLE 26 NO ADDITIVE | 2'42" | 2'29" | 2'23" | 2'43" | 2'30" | 2'24" |
| EXAMPLE 27 DDDMAC | 2'12" | 2'29" | 2'30" | 2'13" | 2'30" | 2'32" |
| EXAMPLE 28 N—CETYL-N,N,N—TRIMETHYL AMMONIUM BROMIDE | 2'51" | 2'33" | 2'19" | 2'52" | 2'34" | 2'22" |
| EXAMPLE 29 N—CETYL-PRYIDINIUM-CHLORIDE H$_2$O | 2'35" | 2'18" | 2'13" | 2'38" | 2'21" | 2'17" |
| EXAMPLE 30 GLUTARALDEHYDE | 1'57" | 2'27" | 5'58" | 2'15" | 4'35" | 6'08" |
| EXAMPLE 31 CHLORHEXIDINE ACETATE | 2'43" | 2'13" | 2'09" | 2'43" | 2'14" | 2'17" |
| EXAMPLE 32 THYMOL | 2'27" | 2'05" | 2'02" | 2'28" | 2'07" | 2'04" |
| EXAMPLE 33 EUGENOL | 2'27" | 2'13" | 2'22" | 2'29" | 2'17" | 2'23" |

0 W = Zero Storage, 1 W = 1 Week Storage, 2 W = 2 Weeks Storage.
2'42" = 2 Minutes and 42 Seconds.

Glutaraldehyde is considered to have significant detrimental affect on the shelf stability characteristics of the alginate.

EXAMPLE 34

The procedure of Example 4 was repeated except the biocide was bisdequallinium acetate. The diameter of inhibition zone in mm was 11.

What is claimed is:

1. A dental impression material comprising a water soluble salt of alginic acid and a setting reactant, the improvement comprising the addition of a biocide comprising about 0.3 to about 6.5 percent by weight of said dental impression material wherein said biocide is didecyldimethyl ammonium chloride.

2. A dental impression material comprising a water soluble salt of alginic acid, a setting reactant, a retarder and fillers, the improvement comprising the addition of a biocide comprising about 0.3 to about 6.5 percent by weight of said dental impression material wherein said biocide is didecyldimethyl ammonium chloride.

3. In a dental impression material comprising a water soluble salt of alginic acid, a setting reactant, a retarder, fillers, a surface hardening agent and a non-volatile, non-aqueous compound to prevent fine powders from dusting during dispensing, measuring and mixing, the improvement comprising the addition of a biocide comprising didecyldimethyl ammonium chloride in the amount of about 0.3 to about 6.5 percent by weight of said dental impression material.

4. The dental impression material of claim 2 wherein said biocide comprises about 0.3 to about 6.5 percent by weight, said alginic acid salt comprises about 5 to about 20 percent by weight, said filler comprises about 40 to about 70 percent by weight and said setting reactant comprises about 8 to about 30 percent by weight and said retarder comprises about 0.5 to about 10 percent by weight.

5. The dental impression material of claim 2 wherein said alginate and said biocidal component are included in a dry powder precursor composition.

6. The dental impression material of claim 2 in the form of a set dental impression.

7. The dental impression material of claim 3 wherein said biocide comprises
about 0.3 to about 6.5 percent by weight, said alginic acid salt
comprises about 5 to about 20 percent by weight, said filler comprises about 40 to about 70 percent by weight and said setting reactant comprises about 8 to about 30 percent by weight and said retarder comprises about 0.5 to about 10 percent by weight.

8. The dental impression material of claim 3 wherein said alginate and said biocidal component are included in a dry powder precursor composition.

9. The dental impression material of claim 3 in the form of a set dental impression.

* * * * *